(12) United States Patent
Yasuda et al.

(10) Patent No.: US 9,945,584 B2
(45) Date of Patent: Apr. 17, 2018

(54) HEATING TOOL

(71) Applicant: Kobayashi Pharmaceutical Co., Ltd., Osaka-shi (JP)

(72) Inventors: Yuki Yasuda, Osaka (JP); Hiromichi Tanaka, Osaka (JP); Daisuke Nishioka, Osaka (JP)

(73) Assignee: Kobayashi Pharmaceutical Co., Ltd., Osaka-shi (JP)

( * ) Notice: Subject to any disclaimer, the term of this patent is extended or adjusted under 35 U.S.C. 154(b) by 451 days.

(21) Appl. No.: 14/418,578

(22) PCT Filed: Jul. 29, 2013

(86) PCT No.: PCT/JP2013/070497
§ 371 (c)(1),
(2) Date: Jan. 30, 2015

(87) PCT Pub. No.: WO2014/021269
PCT Pub. Date: Feb. 6, 2014

(65) Prior Publication Data
US 2015/0211766 A1    Jul. 30, 2015

(30) Foreign Application Priority Data
Aug. 1, 2012 (JP) .................................. 2012-171066

(51) Int. Cl.
*F24J 1/00* (2006.01)
*A61F 7/03* (2006.01)
*A61F 7/02* (2006.01)

(52) U.S. Cl.
CPC ................. *F24J 1/00* (2013.01); *A61F 7/034* (2013.01); *A61F 2007/026* (2013.01);
(Continued)

(58) Field of Classification Search
CPC ..... F24J 1/00; A61F 7/034; A61F 2007/0226; A61F 2007/0036; A61F 2007/0026;
(Continued)

(56) References Cited

U.S. PATENT DOCUMENTS 3,980,070 A    9/1976  Krupa
4,167,561 A *  9/1979  Lamberti ............... A01N 59/00
                                                    424/665

(Continued)

FOREIGN PATENT DOCUMENTS

CN    1181482 A    5/1998
CN    1230670 A   10/1999
(Continued)

OTHER PUBLICATIONS

Office Action dated May 31, 2016, issued for the corresponding JP patent application No. 2012-171066 and English translation thereof.
(Continued)

*Primary Examiner* — Alfred Basichas
(74) *Attorney, Agent, or Firm* — Locke Lord LLP

(57) ABSTRACT

The present invention provides an excellent heating tool in which the generation of unpleasant odors is suppressed. The present invention also provides an excellent heating tool in which changes in aroma are suppressed. The present invention further provides an excellent heating tool in which the generation of unpleasant odors and changes in aroma are suppressed even after storage. The present invention provides a method for suppressing the generation of unpleasant odors and changes in aroma in a heating tool. The present invention provides a heating tool comprising an exothermic composition containing a metal ion sequestrant, an oxidizable metal powder, a water-soluble salt, and water, wherein at least the exothermic composition is housed in an air-permeable container bag.

20 Claims, 1 Drawing Sheet

(52) U.S. Cl.
CPC . *A61F 2007/0226* (2013.01); *A61F 2007/036* (2013.01); *A61F 2007/038* (2013.01)

(58) Field of Classification Search
CPC ...... A61F 2007/0038; A61F 2007/0003; A61F 2007/0011; A61F 2007/0023; A61F 2007/0233; A61F 2007/003; A61F 2007/0032; A61F 2007/0042; A61F 2007/0024
See application file for complete search history.

(56) References Cited

U.S. PATENT DOCUMENTS

| | | |
|---|---|---|
| 5,882,885 A | 3/1999 | Burnham |
| 2004/0042965 A1 | 3/2004 | Usui et al. |
| 2006/0154006 A1* | 7/2006 | Usui ............... A61F 7/034 428/34.1 |
| 2008/0206549 A1 | 8/2008 | Dodo |

FOREIGN PATENT DOCUMENTS

| | | |
|---|---|---|
| CN | 1378433 A | 11/2002 |
| CN | 102492401 A | 6/2012 |
| JP | 05-194952 A | 8/1993 |
| JP | 05-279595 A | 10/1993 |
| JP | 06-064912 A | 3/1994 |
| JP | 11-049627 A | 2/1999 |
| JP | 11-137275 A | 5/1999 |
| JP | 11-181433 A | 7/1999 |
| JP | 2000-060887 A | 2/2000 |
| JP | 2001-137273 A | 5/2001 |
| JP | 2001-137275 A | 5/2001 |
| JP | 2001-212166 A | 8/2001 |
| JP | 2001-218816 A | 8/2001 |
| JP | 2002-155273 A | 5/2002 |
| JP | 2002-204833 A | 7/2002 |
| JP | 2003-129041 A | 5/2003 |
| JP | 2004-065949 A | 3/2004 |
| JP | 2006-223851 A | 8/2006 |
| JP | 2007-154105 A | 6/2007 |
| JP | 2010-051690 A | 3/2010 |
| JP | 2012-140537 A | 7/2012 |
| WO | 01/26528 A1 | 4/2001 |
| WO | WO-2006/006656 A1 | 1/2006 |
| WO | 2009/156907 A2 | 12/2009 |

OTHER PUBLICATIONS

Office Action dated Jan. 4, 2017 for JP patent application No. 2012-171066 and English translation thereof.
Office Action dated Nov. 27, 2015 for CN Patent Application No. 201380051644.7.
International Search Report dated Sep. 10, 2013, issued for PCT/JP2013/070497.
Supplementary European Search Report dated Mar. 15, 2016, issued for the European patent application No. 13825934.6.

* cited by examiner

HEATING TOOL

TECHNICAL FIELD

The present invention relates to a heating tool. More specifically, the present invention relates to a heating tool in which the generation of unpleasant odors and changes in aroma are suppressed. The present invention also relates to a method for suppressing the generation of unpleasant odors and changes in aroma in a heating tool.

BACKGROUND ART

Hitherto, disposable body warmers have been frequently used because they have excellent properties as a warming tool for the body, such as portability, safety, and convenience, and also because they are inexpensive. Typical disposable body warmers use an exothermic composition that generates heat in the presence of air, and a heat-keeping effect is produced through this heat-generating mechanism. However, the disposable body warmers generate characteristic odors attributable to the exothermic composition; this has been a cause of unpleasant odors specific to disposable body warmers.

Hitherto, perfuming of disposable body warmers and other heating tools has been reported. For example, Patent Literature 1 discloses adding a fragrance to the surface of a hitherto-known disposable body warmer, and promoting the volatilization and diffusion of the fragrance by utilizing the heat-generating mechanism of disposable body warmers. However, when a fragrance is added as above to a heating tool that uses a disposable body warmer, aroma originating from the fragrance changes, posing a problem in which the desired aroma cannot be fully enjoyed.

A heating tool to which aroma is imparted generates unpleasant odors attributable to the exothermic composition as the aroma changes. It is thus necessary to suppress the generation of unpleasant odors while maintaining a favorable aroma.

Additionally, heating tools are not only used immediately after their production, but also often used after a certain period of storage time. It is thus also important to suppress the generation of unpleasant odors and changes in aroma that occur during storage.

CITATION LIST

Patent Literature

PTL 1: JP2001-218816A

SUMMARY OF INVENTION

Technical Problem

In view of the above, an object of the present invention is to provide an excellent heating tool in which the generation of unpleasant odors is suppressed. Another object of the present invention is to provide an excellent heating tool in which changes in aroma are suppressed. It is still another object of the present invention is to provide an excellent heating tool in which the generation of unpleasant odors and changes in aroma are suppressed even after storage. It is still yet another object of the present invention to provide a method for suppressing the generation of unpleasant odors and/or changes in aroma in a heating tool.

Solution to Problem

The present inventors conducted extensive research to achieve the above objects, and found that the use of a metal ion sequestrant in a heating tool can suppress the generation of unpleasant odors, as well as changes in aroma in the heating tool even after storage. The present inventors conducted further research based on this finding, and thereby accomplished the present invention. More specifically, the present invention provides the following:

Item 1. A heating tool comprising an exothermic composition containing a metal ion sequestrant, an oxidizable metal powder, a water-soluble salt, and water, wherein at least the exothermic composition is housed in an air-permeable container bag.

Item 2. The heating tool according to Item 1, further comprising an oxidation accelerator and/or a water-retaining agent.

Item 3. The heating tool according to Item 1 or 2, further comprising a fragrance.

Item 4. The heating tool according to any one of Items 1 to 3, wherein the metal ion sequestrant is at least one member selected from the group consisting of aminocarboxylic acid-based metal ion sequestrants, phosphonic acid-based metal ion sequestrants, condensed phosphoric acid-based metal ion sequestrants, carboxylic acid-based metal ion sequestrants, and substances having an ability to adsorb metal ions.

Item 5. The heating tool according to any one of Items 1 to 4, wherein the proportion of the metal ion sequestrant in the exothermic composition is 0.0001 to 10 wt %.

Item 6. The heating tool according to any one of Items 2 to 5, wherein the oxidation accelerator is at least one member selected from the group consisting of carbon black, graphite, activated carbon, coal, charcoal, bamboo charcoal, acetylene black, and charcoal made from waste coffee grounds.

Item 7. The heating tool according to any one of Items 2 to 6, wherein the oxidation accelerator has an iodine adsorption of not higher than 400 mg/g on average.

Item 8. The heating tool according to any one of Items 2 to 7, wherein the oxidation accelerator has electrical conductivity.

Item 9. The heating tool according to any one of Items 1 to 8, wherein the amount of the metal ion sequestrant contained in the exothermic composition is 0.0002 to 20 parts by weight per 100 parts by weight of the oxidizable metal powder.

Item 10. The heating tool according to any one of Items 2 to 9, wherein the proportion of the oxidation accelerator in the exothermic composition is 1 to 30 wt %.

Item 11. The heating tool according to any one of Items 3 to 10, wherein the fragrance is contained in an amount of 0.0001 to 20 parts by weight per 100 parts by weight of the exothermic composition.

Item 12. The heating tool according to any one of Items 3 to 11, wherein the fragrance is contained in an amount of 0.0003 to 500 parts by weight per 100 parts by weight of the oxidation accelerator contained in the exothermic composition.

Item 13. The heating tool according to any one of Items 3 to 12, wherein the fragrance is (1) housed in an air-permeable container bag;

(2) contained in at least a portion of the air-permeable container bag; or (3) contained in a sheet or an adhesive component, or housed in a container bag other than the air-permeable container bag, the seat, the adhesive component, or the container bag other than the air-permeable container bag being disposed inside and/or outside the air-permeable container bag.

Item 14. The heating tool according to any one of Items 3 to 13, wherein the fragrance is housed in the air-permeable container bag.

Item 15. The heating tool according to any one of Items 3 to 14, wherein the fragrance is supported on a carrier.

Item 16. A method for suppressing the generation of unpleasant odors and/or changes in aroma in a heating tool, the method comprising a step of housing an exothermic composition containing a metal ion sequestrant, an oxidizable metal powder, a water-soluble salt, and water in an air-permeable container bag.

Item 17. The method according to Item 16, the method comprising a step of housing an exothermic composition containing a metal ion sequestrant, an oxidizable metal powder, a water-soluble salt, water, and an oxidation accelerator and/or a water-retaining agent in an air-permeable container bag.

Item 18. The method according to Item 16 or 17, the method further comprising a step of incorporating a fragrance into the heating tool.

Item 19. A method for suppressing the generation of unpleasant odors and/or changes in aroma in a heating tool by using the heating tool of any one of Items 1 to 15.

Item 20. The heating tool according to any one of Items 1 to 15, wherein the heating tool is used in a method for suppressing the generation of unpleasant odors and/or changes in aroma in a heating tool.

Item 21. Use of the heating tool of any one of Items 1 to 15 in the production of a heating tool in which the generation of unpleasant odors and/or changes in aroma are suppressed.

Advantageous Effects of Invention

The heating tool of the present invention can effectively suppress the generation of unpleasant odors attributable to the exothermic composition. According to the present invention, even when the heating tool contains a fragrance, changes in aroma originating from the fragrance can be suppressed so that the desired aroma can be maintained. Further, according to the present invention, even when the heating tool is used after storage, the generation of unpleasant odors can be effectively suppressed, excellent aromatic properties can be achieved, and exothermic effects sufficient as a heating tool can be obtained.

BRIEF DESCRIPTION OF DRAWINGS

FIG. 1 is an example of a heating tool containing a fragrance, which is mixed with an exothermic composition.

FIG. 2 is an example of a heating tool containing a fragrance, which is present in an adhesive component.

FIG. 3 is an example of a heating tool containing a fragrance, which is mixed with an exothermic composition.

FIG. 4 is an example of a fragrance-free heating tool.

DESCRIPTION OF EMBODIMENTS

Figure 1:
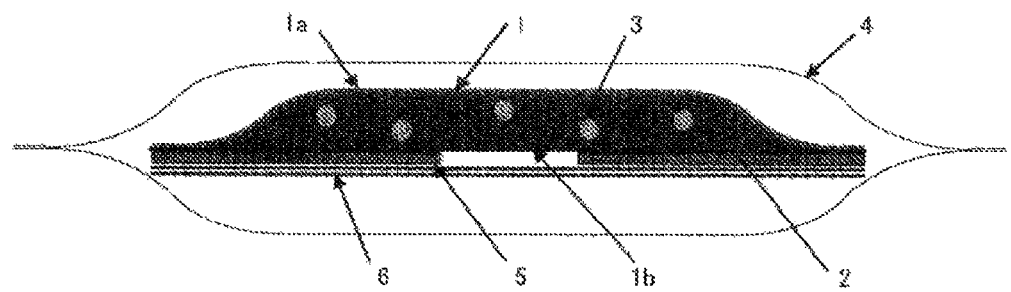
FIG. 1 is an example of a stick-on type heating tool packaged in an outer bag. The air-permeable container bag illustrated in FIG. 1 is a model drawing of a container bag having an air-permeable portion at one side and an air-impermeable portion at the other side.

The heating tool of the present invention has a feature in that it comprises an exothermic composition containing a metal ion sequestrant, an oxidizable metal powder, a water-soluble salt, and water, and that at least the exothermic composition is housed in an air-permeable container bag. The heating tool of the present invention is described below. In this specification, the terms "comprise," "comprising," "contain," and "containing" include both the meanings of "consist essentially of" and "consist of."

Exothermic Composition

The heating tool of the present invention comprises an exothermic composition. The exothermic composition generates heat in the presence of oxygen, and contains a metal ion sequestrant, an oxidizable metal powder, a water-soluble salt, and water.

—Metal Ion Sequestrant

The metal ion sequestrant is not limited as long as it is a substance having an ability to sequester metal ions, and a substance with two or more coordinations and having an ability to bind to metal ions by the ligand, a substance having an ability to electrically adsorb metal ions, a substance having an ability to physically adsorb metal ions in the micropores, a substance having an ability to sequester metal ions, and combinations of these substances may be used. Hitherto known metal ion sequestrants are one example of these substances. More specific examples include metal ion sequestrants, such as aminocarboxylic acid-based metal ion sequestrants, such as ethylenediaminetetraacetic acid, nitrilotriacetic acid, diethylenetriaminepentaacetic acid, hydroxyethylenediaminetetraacetic acid, hydroxyethylenediaminetriacetic acid, triethylenetetraminehexaacetic acid, 1,3-propanediaminetetraacetic acid, 1,3-diamino-2-hydroxypropane tetraacetic acid, hydroxyethyliminodiacetic acid, glycol etherdiaminetetraacetic acid, dicarboxymethylglutamic acid, and salts thereof;

phosphonic acid-based metal ion sequestrants, such as hydroxyethylidenediphosphonic acid, nitrilotris methylenephosphonic acid, phosphonobutanetricarboxylic acid, ethylenediaminetetramethylene phosphonic acid, diethylenetriaminepentamethylene phosphonic acid, and salts thereof;

condensed phosphoric acid-based metal ion sequestrants, such as tripolyphosphoric acid, pyrophosphoric acid, metaphosphoric acid, and salts thereof;

carboxylic acid-based metal ion sequestrants, such as dihydroxyglycine, dihydroxyethylglycine, citric acid, succinic acid, malic acid, fumaric acid, tartaric acid, malonic acid, maleic acid, ascorbic acid, gluconic acid, and salts thereof; and various substances having an ability to adsorb metal ions, such as zeolite (aluminosilicate), acrylic acid, methacrylic acid, bipyridine, phenanthroline, porphyrin, phthalocyanine, corrole, chlorin, and crown ether.

Examples of these salts include alkali metal salts, such as sodium and potassium; alkaline earth metal salts, such as magnesium and calcium; and hitherto known salts, such as ammonium salts and amine salts.

As a metal ion sequestrant, it is preferable to use aminocarboxylic acid-based metal ion sequestrants, condensed phosphoric acid-based metal ion sequestrants, and carboxylic acid-based metal ion sequestrants, and it is more preferable to use aminocarboxylic acid-based metal ion sequestrants and carboxylic acid-based metal ion sequestrants.

Of these, as metal ion sequestrants, it is furthermore preferable to use ethylenediaminetetraacetic acid, nitrilotriacetic acid, tripolyphosphoric acid, pyrophosphoric acid, citric acid, malic acid, and salts thereof, and it is particularly preferable to use ethylenediaminetetraacetic acid, citric acid, and salts thereof.

These may be used singly, or in a combination of two or more.

The amount of the metal ion sequestrant is not limited as long as the desired effects are obtained. The proportion of the metal ion sequestrant in the exothermic composition is, for example, 0.0001 to 10 wt %, preferably 0.001 to 7 wt %, and more preferably 0.01 to 5 wt %.

The amount of the metal ion sequestrant is not limited as long as the desired effects are obtained. The amount of the metal ion sequestrant contained in the exothermic composition is, for example, 0.0002 to 20 parts by weight, preferably 0.002 to 15 parts by weight, and more preferably 0.02 to 10 parts by weight, per 100 parts by weight of the oxidizable metal powder mentioned later.

The metal ion sequestrant is not limited as long as the effects of the present invention are obtained, and may be contained in the exothermic composition as a single component for sequestering metal ions. To more effectively achieve the effects of the present invention, it is preferable to dissolve the metal ion sequestrant in water beforehand to allow the metal ion sequestrant to be supported on at least any one of the components other than the oxidizable metal powder contained in the exothermic composition by impregnation or the like.

—Oxidizable Metal Powder

The oxidizable metal powder contained in the exothermic composition is not limited as long as it is a metallic powder that generates heat when being oxidized. Examples thereof include iron powder, zinc powder, aluminum powder, magnesium powder, and copper powder. A preferable example is iron powder. Examples of the iron powder include reduced iron powder, cast-iron powder, atomized iron powder, and electrolytic-iron powder. These may be used singly, or in a combination of two or more.

The oxidizable metal powder may be powdery, granular, or fibrous. These may be used singly, or in a combination of two or more.

Although it is not limited as long as the desired effects are obtained, from the standpoint of comfort when the heating tool is attached to the body, the heat generation efficiency, and the like, the oxidizable metal powder has an average particle diameter of, for example, 0.01 to 1000 μm, preferably 0.1 to 500 μm, and more preferably 0.5 to 300 μm. The average particle diameter of oxidizable metal powder can be measured by, for example, a JIS method that uses a standard sieve.

The amount of the oxidizable metal powder is not limited as long as the desired effects are obtained. The proportion of the oxidizable metal powder in the exothermic composition is, for example, 20 to 80 wt %, preferably 40 to 70 wt %, and more preferably 45 to 60 wt %.

—Water-Soluble Salt

The water-soluble salt is contained in the exothermic composition to promote the oxidation of the oxidizable metal powder. The water-soluble salt is not limited as long as the desired effects are obtained. Preferable examples of the water-soluble salt include hydrochlorides and sulfates of alkali metals such as sodium and potassium; hydrochlorides and sulfates of alkaline earth metals such as calcium and magnesium; and hydrochlorides and sulfates of metals such as iron, copper, aluminum, zinc, nickel, silver, and barium. More preferable examples thereof include potassium chloride, sodium chloride, and the like. These may be used singly, or in a combination of two or more.

The amount of water-soluble salt is also not limited as long as the desired effects are obtained. The proportion of the water-soluble salt in the exothermic composition is, for example, 0.1 to 20 wt %, preferably 0.1 to 10 wt %, more preferably 0.5 to 10 wt %, still more preferably 0.5 to 7 wt %, and particularly preferably 1 to 5 wt %.

—Water

Usable water includes distilled water, tap water, ion exchange water, pure water, ultrapure water, industrial water, and the like.

The amount of water is also not limited as long as the desired effects are obtained. The proportion of water in the exothermic composition is, for example, 5 to 60 wt %, preferably 10 to 40 wt %, and more preferably 15 to 35 wt %.

As stated above, the exothermic composition contains a metal ion sequestrant, an oxidizable metal powder, a water-soluble salt, and water. In this manner, the generation of unpleasant odors attributable to the exothermic composition can be effectively suppressed while the exothermic composition generates heat to increase the temperature of the heating tool to a temperature preferable as a heating tool (e.g., about 32 to 85° C., measurement value according to JIS S4100 (2007)).

In addition to the components mentioned above, the exothermic composition may further optionally contain other components that can be contained in an exothermic composition. Examples of such components include, but are not limited to, oxidation accelerators, water-retaining agents, surfactants, hydrogen-generating inhibitors, thickening agents, and excipients. Of these components, for example, oxidation accelerators and water-retaining agents are described below.

—Oxidation Accelerator

The oxidation accelerator contained in the exothermic composition is used for the purpose of further promoting the supply of oxygen to the exothermic composition, in particular, to the oxidizable metal powder, by air intake. The oxidation accelerator is not limited as long as oxygen can be supplied. Examples of the oxidation accelerator include carbon black, graphite, activated carbon, coal, charcoal, bamboo charcoal, acetylene black, and charcoal made from waste coffee grounds. Of these, carbon black, activated carbon, bamboo charcoal, charcoal, and charcoal made from waste coffee grounds are preferable, and carbon black, activated carbon, and bamboo charcoal are more preferable. These may be used singly, or in a combination of two or more.

Although it is not limited as long as the desired effects are obtained, from the standpoint of comfort when the heating tool is attached to the body, the oxygen supply efficiency, and the like, the oxidation accelerator is preferably in, for example, a powdery, granular, or fibrous form. These may be used singly, or in a combination of two or more. The oxidation accelerator has an average particle diameter of, for example, 0.001 to 1000 μm, preferably 0.005 to 500 μm, and more preferably 0.01 to 200 μm.

When the heating tool of the present invention contains a fragrance, it is also possible to use an oxidation accelerator mentioned above. To effectively sustain the aromatic properties of the fragrance for a long period of time, the oxidation accelerator has an iodine adsorption of not higher than 400 mg/g on average. In this case, the oxidation accelerator preferably has an iodine adsorption of not higher than 300 mg/g on average, more preferably not higher than 250 mg/g on average, and particularly preferably not higher than 200 mg/g on average. The lower limit of the iodine adsorption is not particularly limited, but is theoretically, for example, 0 mg/g on average. When two or more oxidation accelerators are used in combination, the average of the iodine adsorption of the combination (e.g., mixture) preferably satisfies the above-mentioned values. The iodine adsorption is measured and calculated by the method defined in JIS K1474. Examples of oxidation accelerators having an iodine adsorption of not higher than 400 mg/g on average include, but are not limited to, carbon black, charcoal, bamboo charcoal, charcoal made from waste coffee grounds, and the like.

The heating tool of the present invention may generate heat so that the temperature of the heating tool is increased to a value preferable for the application to the skin. The temperature is, for example, about 32 to 85° C., and more preferably about 40 to 70° C. (measurement value based on JIS S4100 (2007)). To allow the heating tool to further efficiently generate heat to increase the temperature of the heating tool to a more preferable value, the oxidation accelerator preferably has electrical conductivity. Oxidation accelerators having or not having electrical conductivity are known. Examples of known oxidation accelerators having electrical conductivity equal to or higher than a certain level include, but are not limited to, carbon black, graphite, activated carbon, and the like.

In the present invention, the heat-generation temperature of the heating tool is measured according to JIS S4100 (2007). More specifically, predetermined underlay material and covering material are laid on a warming portion defined in JIS S4100 (2007). The warming portion is heated to 30° C., and held within one degree of that temperature. Meanwhile, the heating tool left for 2 or more hours in an atmosphere having the same temperature as the ambient temperature is caused to generate heat based on the method of use. In accordance with a predetermined method, measurement is performed by measuring the time etc., required from the start of heat generation to returning to a predetermined temperature after exceeding the predetermined temperature and reaching the maximum temperature.

The amount of the oxidation accelerator is not limited as long as the desired effects are obtained. The proportion of the oxidation accelerator in the exothermic composition is preferably, for example, 1 to 30 wt %, preferably 3 to 25 wt %, and more preferably 5 to 23 wt %.

The amount of the oxidation accelerator relative to the oxidizable metal powder described later is also not limited as long as the desired effects are obtained. The amount of the oxidation accelerator is, for example, 2 to 60 parts by weight, preferably 5 to 50 parts by weight, and more preferably 10 to 40 parts by weight, per 100 parts by weight of the oxidizable metal powder.

—Water-Retaining Agent

The water-retaining agent has a function of retaining water, and is not limited as long as it has the function and can produce desired effects. Examples thereof include porous substances, water-absorbing resins, and the like. Examples of the water-retaining agent include natural and synthetic inorganic substances such as vermiculite, perlite, calcium silicate, kaolin, talc, smectite, mica, bentonite, calcium carbonate, silica gel, alumina, zeolite, silicon dioxide, diatomaceous earth, and aluminum oxide; and natural and synthetic organic substances such as pulp, wood flour (sawdust), cotton, polyacrylate-based resins, polysulfonate-based resins, maleic anhydride salt-based resins, polyacrylamide-based resins, polyvinyl alcohol-based resins, polyethylene oxide-based resins, polyaspartate-based resins, polyglutamate-based resins, poly alginate-based resins, starches, and cellulose. Preferable examples thereof include vermiculite, perlite, silica gel, diatomaceous earth, aluminum oxide, wood flour (sawdust), and polyacrylate-based resins. These may be used singly, or in a combination of two or more.

Although not limited as long as the desired effects are obtained, an example of the average particle diameter of the water-retaining agent is 0.1 to 3000 μm, preferably 0.5 to 1000 μm, and more preferably 1 to 500 μm. The average particle diameter of the water-retaining agent is also measured in a manner similar to the aforementioned method for measuring that of the oxidizable metal powder.

The amount of the water-retaining agent is also not limited as long as the desired effects are obtained. The proportion of the water-retaining agent in the exothermic composition is, for example, 1 to 20 wt %, preferably 3 to 15 wt %, and more preferably 5 to 10 wt %.

In these water-retaining agents, water-retaining agents having a porous structure, especially vermiculite, etc., can serve not only as a water-retaining agent, but also as an air passageway.

In the exothermic composition, the total amount of the metal ion sequestrant, oxidizable metal powder, water-soluble salt, and water is not limited as long as the desired effects are obtained, and the heat-generation temperature in the exothermic composition may be suitably set to be a temperature (e.g., about 32 to 85° C., and preferably about 40 to 70° C. according to JIS S4100) preferable for the heating tool. Further, when the exothermic composition further contains an oxidation accelerator and/or a water-retaining agent, the total amount is not limited as long as the desired effects are obtained, and the heat-generation temperature in the exothermic composition may be suitably set to be a temperature preferable for the heating tool.

Although the present invention is not limited thereto, in one embodiment of the exothermic composition used for the heating tool of the present invention, the amounts of the components in the exothermic composition are, for example, as follows: 0.0001 to 10 wt % for the metal ion sequestrant, 20 to 80 wt % for the oxidizable metal powder, 0.1 to 20 wt % for the water-soluble salt, and 5 to 60 wt % for water.

In another embodiment of the exothermic composition used for the heating tool of the present invention, the amounts of the components in the exothermic composition are, for example, as follows: 0.0001 to 10 wt % for the metal ion sequestrant, 20 to 80 wt % for the oxidizable metal powder, 1 to 30 wt % for the oxidation accelerator, 0.1 to 20 wt % for the water-soluble salt, and 5 to 60 wt % for water.

In another embodiment of the exothermic composition used for the heating tool of the present invention, the amounts of the components in the exothermic composition are, for example, as follows: 0.0001 to 10 wt % for the metal ion sequestrant, 20 to 80 wt % for the oxidizable metal powder, 0.1 to 20 wt % for the water-soluble salt, 1 to 20 wt % for the water-retaining agent, and 5 to 60 wt % for water.

In another embodiment of the exothermic composition used for the heating tool of the present invention, the amounts of the components in the exothermic composition are, for example, as follows: 0.0001 to 10 wt % for the metal ion sequestrant, 20 to 80 wt % for the oxidizable metal powder, 1 to 30 wt % for the oxidation accelerator, 0.1 to 20 wt % for the water-soluble salt, 1 to 20 wt % for the water-retaining agent, and 5 to 60 wt % for water.

In an embodiment of the exothermic composition used for the heating tool of the present invention, the composition contains ethylenediaminetetraacetic acid trisodium salt, iron powder, sodium chloride, and water.

In another embodiment of the exothermic composition used for the heating tool of the present invention, the composition contains ethylenediaminetetraacetic acid trisodium salt, iron powder, carbon black having an iodine adsorption of not higher than 400 mg/g on average and electrical conductivity, sodium chloride, and water.

In another embodiment of the exothermic composition used for the heating tool of the present invention, the composition contains ethylenediaminetetraacetic acid trisodium salt, iron powder, carbon black having an iodine adsorption of not higher than 400 mg/g on average and electrical conductivity, sodium chloride, water-absorbing polymer, vermiculite, and water.

The exothermic composition is prepared by mixing the metal ion sequestrant, oxidizable metal powder, water-soluble salt, water, and, if necessary, other components as described above. The exothermic composition may be prepared in the presence of oxygen, or may be prepared in vacuum or in an inert gas atmosphere. These can be prepared according to a hitherto known procedure for producing a heating tool.

Since the heating tool of the present invention uses a metal ion sequestrant in the heating tool, as described above, the heating tool of the present invention can effectively suppress the generation of unpleasant odors attributable to the exothermic composition. According to the present invention, even when the heating tool contains a fragrance, changes in or loss of aroma originating from the fragrance can be suppressed so that the desired aroma can be maintained. Further, according to the present invention, even when the heating tool is used after storage, the generation of unpleasant odors can be effectively suppressed, excellent aromatic properties can be achieved, and exothermic effects sufficient as a heating tool can be obtained.

Air-Permeable Container Bag for Housing Exothermic Composition

In the heating tool of the present invention, the exothermic composition is housed in an air-permeable container bag for housing the exothermic composition (hereinafter, sometimes described as "container bag for the exothermic composition"). The air-permeable container bag for housing the exothermic composition is capable of housing the exothermic composition, and is not limited as long as it has air-permeability; a hitherto known container bag can be used. For example, as the container bag for the exothermic composition, from the standpoints of preventing leakage of the exothermic composition, having durability against the heat generation by the exothermic composition, and improving the ease of use of the heating tool, etc., an air-permeable bag and the like used in hitherto known disposable body warmers can, for example, be used.

In a more specific non-limiting example, the container bag for the exothermic composition has a laminated structure in which an air-permeable resin film is laminated on an air-permeable woven fabric or nonwoven fabric. In this case, the air-permeable resin film is arranged on the inside of the container bag for the exothermic composition, and the air-permeable woven fabric or nonwoven fabric is arranged on the outside of the container bag for the exothermic composition.

The resin used for the air-permeable resin film is not particularly limited; however, preferable examples thereof include thermoplastic resins. Examples of the thermoplastic resins include polyethylene, polypropylene, polyester, polyamide, polyurethane, polystyrene, polyvinyl alcohol, polyvinyl chloride, polyvinylidene chloride, polycarbonate, ethylene-vinyl acetate copolymers, and the like. From the standpoint of usage of the heating tool as being attached to the body, preferable examples of the thermoplastic resin include polyethylene, polypropylene, ethylene-vinyl acetate copolymers, and the like. These may be used singly, or in a combination of two or more.

In the air-permeable resin film used in the present invention, pores for ensuring the air permeability in the resin film formed by the resin are provided at least partially. The pores allow air to move in and out of the container bag for the exothermic composition, and are not limited as long as they are of sufficient size to prevent leakage of the exothermic composition to the outside of the container bag. Further, the sensible temperature of the heating tool upon usage can be affected by the air permeability of the container bag for the exothermic composition; therefore, the size, shape, and number of the pores may be suitably determined considering the sensible temperature of the heating tool upon usage. Means for forming pores in the resin film are hitherto known, and a known procedure can be followed.

Examples of the fiber materials of the air-permeable woven fabric or nonwoven fabric include synthetic fibers such as nylon, vinylon, polyester, rayon, acrylic, polyethylene, polypropylene, acetate, polyvinyl chloride, and polybutylene terephthalate, natural fibers such as cotton, hemp, silk, and paper, mixed fibers of synthetic fibers and natural fibers, and the like. From the perspective of sense of use, examples of the fiber materials include nylon, polyester, polypropylene, and the like, and more preferably nylon and polyester. These may be used singly, or in a combination of two or more. The woven fabric or nonwoven fabric is not limited as long as the fabric allows air to move in and out of the container bag for the exothermic composition, and can prevent leakage of the exothermic composition to the outside of the container bag. The weight per area of the fabric is, for example, preferably 25 to 70 g/m$^2$.

The laminate of the air-permeable resin film and air-permeable woven fabric or nonwoven fabric is not limited as long as the obtained laminate is strong enough to serve as the container bag for the exothermic composition, and ensures air permeability. The laminate can be formed by, for example, a lamination method. Examples of the lamination method include methods of laminating by thermal bond, and methods of laminating using adhesives such as hot-melt adhesives, acrylic adhesives, or urethane adhesives. These laminates may be formed partially or entirely on the surface of the container bag for the exothermic composition, as long as the desired effects are obtained.

Commercially available products may be used as the container bag for the exothermic composition.

The size and shape of the container bag for the exothermic composition are also not limited as long as the desired effects are obtained, and may be suitably determined depending on the purpose of use.

For example, when the heating tool of the present invention is attached to clothing, skin, or the like to be used, an adhesive sheet for fixing the heating tool of the present invention on the clothing, skin, or the like with a peelable force can be provided on the outside of the container bag for the exothermic composition. Usable examples of such an adhesive sheet include hitherto known adhesive sheets used for so-called stick-on type disposable body warmers, and hitherto known skin-direct stick-on type adhesive sheets.

Fragrance

The heating tool of the present invention may contain a fragrance. The fragrance may be suitably determined depending on the use and preference, and is not limited. Natural fragrances such as essential oils can be used singly or in combination, or synthetic single fragrances can be used singly or in combination. Natural fragrances and synthetic fragrances can also be freely combined to be used as a compound fragrance. Examples of the natural fragrances (essential oils) include, but are not limited to, vanilla, lavender, chamomile, rosemary, sage, citronella, ginger, ylang-ylang, eucalyptus, mint, rose, lily, lilac, jasmine, cardamom, lemon grass, yuzu, orange, lemon, lime, grapefruit, neroli, cedar wood, sandalwood, anise, caraway, amber, musk, civet, castoreum, and the like. Examples of the synthetic single fragrances include, but are not limited to, acetophenone, aldehyde $C_6$-$C_{16}$, allyl caproate, amylcinnamic aldehyde, amyl salicylate, benzaldehyde, benzyl acetate, benzyl alcohol, borneol, camphor, cinnamic alcohol, citral, citronellal, citronellol, coumarin, damascone, dehydrolinalool, dihydromyrcenol, diphenyl oxide, ethyl-2-methyl butyrate, ethyl butyrate, eugenol, geraniol, geranyl acetate, phenylethyl alcohol, hedione, hexanol, cis-3-hexanol, α-hexyl cinnamic aldehyde, isoamyl acetate, lilial, limonene, linalool, linalyl acetate, l-menthol, methyl benzoate, methyl ionone, methyl salicylate, nerol, α-pinene, β-pinene, rose oxide, terpineol, γ-nonalactone, γ-undecalactone, vanillin, and the like. Since aromatic properties can be enhanced by the heat generated in the heating tool, as the fragrance, a fragrance that can vaporize at a temperature (e.g., about 32 to 85° C.) at which the exothermic composition generates heat in the presence of air is more preferable. The fragrance may be liquid, solid, or the like.

The amount of the fragrance in the heating tool of the present invention is not limited as long as the desired effects are obtained. The amount of the fragrance is, for example, 0.0001 to 10 parts by weight, preferably 0.001 to 7 parts by weight, and more preferably 0.01 to 5 parts by weight, per 100 parts by weight of the exothermic composition.

The amount of the fragrance is, for example, 0.0001 to 20 parts by weight, preferably 0.001 to 15 parts by weight, and more preferably 0.01 to 10 parts by weight, per 100 parts by weight of the oxidizable metal powder in the exothermic composition.

When the exothermic composition contains the oxidation accelerator, the amount of the fragrance is, for example, 0.0003 to 500 parts by weight, preferably 0.03 to 100 parts by weight, and more preferably 0.17 to 50 parts by weight, per 100 parts by weight of the oxidation accelerator in the exothermic composition.

When a fragrance is contained in the heating tool, how the fragrance is contained in the heating tool of the present invention is not limited as long as aroma can be imparted to the heating tool, and the fragrance may be further housed in the air-permeable container bag, or may exist outside the container bag.

More specifically, regarding how the fragrance is contained in the heating tool of the present invention, the fragrance may, for example, be mixed with the components of the exothermic composition and housed in the container bag; the fragrance may be contained in at least a portion of the container bag for the exothermic composition; or the fragrance may be contained beforehand in another sheet or in an optional adhesive component, etc., or housed in another air-permeable container bag or the like, and the sheet, the adhesive component, or the container bag, etc., may be disposed inside and/or outside of the container bag for the exothermic composition.

When the fragrance is mixed with the components in the exothermic composition, the fragrance itself, for example, may be mixed with the components; a mixture obtained by mixing water, etc., with the fragrance by using a surfactant or the like may be mixed with the components; the fragrance or the mixture may be encapsulated beforehand in hitherto known microcapsules, and the obtained encapsulated microcapsules may be mixed with the components; or the fragrance or the mixture may be supported on a carrier, and then mixed with the components. From the standpoint of preventing adhesion of the fragrance to the components in the exothermic composition as much as possible, and particularly from the standpoint of preventing adhesion of the fragrance to the oxidation accelerator and the oxidizable metal powder as much as possible, the fragrance is, for example, preferably supported on a carrier beforehand, and then mixed with the components. Examples of the carrier include, but not limited to unless the effects of the present invention are hindered, silica, vermiculite, perlite, fluorite, zeolite, fine silicon dioxide, pulp, plastics, rubbers, and elastomers. The particle diameter of the carrier is also not limited, unless the effects of the present invention are hindered. An example of the average particle diameter is about 0.1 to 3000 μm, preferably about 0.5 to 1000 μm, more preferably about 1 to 500 μm. The amount of the carrier is also not limited unless the effects of the present invention are hindered.

When supporting the fragrance, for example, the fragrance may be supported on the components contained in the exothermic composition. From the standpoint of the influence on heat generation, the fragrance is preferably supported on components other than the metal ion sequestrant and oxidizable metal powder in the exothermic composition, and preferably supported on components other than the metal ion sequestrant, oxidizable metal powder, and oxidation accelerator when the exothermic composition contains an oxidation accelerator. For example, when the exothermic composition contains a water-retaining agent, the fragrance may be preferably supported on the water-retaining agent contained in the exothermic composition.

As described above, when the fragrance is contained in at least a portion of the container bag for the exothermic composition, the container bag may, for example, be impregnated with the fragrance beforehand, or the fragrance may be kneaded beforehand into at least one of the film, the woven fabric, and the nonwoven fabric constituting the container bag. As another example, when the fragrance is contained in at least a portion of the container bag for the exothermic composition, the fragrance may be encapsulated in microcapsules, and these may be deposited on at least one of the film, woven fabric, and nonwoven fabric constituting the container bag.

As described above, when the fragrance is contained beforehand in another sheet or in an optional adhesive component, etc., or housed in another air-permeable container bag, etc., and the sheet, the adhesive component, or the container bag, etc., is disposed inside and/or outside of the container bag for the exothermic composition, examples of the sheet and the adhesive component, etc., include hitherto known adhesive sheets used for so-called stick-on type disposable body warmers, skin-direct stick-on type adhesive sheets, and adhesive components, etc., used therefor. The air-permeable container bag in which the fragrance is housed beforehand is, for example, a container bag similar to the aforementioned container bag for the exothermic composition.

Since the heating tool of the present invention uses the metal ion sequestrant, even when the heating tool contains a fragrance, changes in or loss of aroma originating from the fragrance can be suppressed while suppressing odors attributable to the exothermic composition, thus maintaining desired aroma. Further, according to the present invention, even when the heating tool is used after storage, unpleasant odors can be effectively suppressed as described above, and excellent aromatic properties originating from the fragrance can thus be exhibited. Furthermore, according to the heating tool of the present invention, exothermic effects sufficient as a heating tool can be exhibited even when a fragrance is contained.

The present invention is not limited to the following; however, when a fragrance and an oxidation accelerator are contained, excellent aromatic properties originating from the fragrance can be effectively attained while suppressing the odors attributable to the exothermic composition by using an oxidation accelerator having an iodine adsorption of not higher than 400 mg/g on average. When an oxidation accelerator having an iodine adsorption of not higher than 400 mg/g on average is used, even when the fragrance and the exothermic composition exist in contact with each other in the heating tool of the present invention, loss or changes of the aromatic properties during storage can be more effectively suppressed or prevented as long as the heating tool is stored in an environment preventing contact with oxygen.

Furthermore, when the fragrance is a fragrance, such as lavender or chamomile, having a relaxing effect, the heating tool having such a fragrance is considered to further have a relaxing effect. When the fragrance contained in the heating tool of the present invention is a fragrance, such as eucalyptus oil, having an insect-repelling effect, the heating tool of the present invention is considered to further have an insect-repelling effect. Accordingly, the heating tool of the present invention is considered to have additional effects (functions) depending on the characteristics of the fragrance to be used. The effects (functions) of the fragrances are hitherto known.

The heating tool of the present invention may contain optional components in addition to the fragrance. Examples of such components include insect-repelling components such as pyrethroid and paramenthane, and other relaxing components including warm-sensation components such as capsicum extract and nonylic acid vanillyl amide, and cool-sensation components such as the aforementioned l-menthol and camphor. Such optional components can be contained within a range that does not hinder the effects of the present invention. The amounts of these components may be suitably set within a range that does not hinder the effects of the present invention.

Heating Tool

The heating tool of the present invention comprises the exothermic composition, wherein at least the exothermic composition is housed in a container bag having air permeability. The heating tool of the present invention is produced by housing the exothermic composition prepared as described above in the aforementioned air-permeable container bag, if necessary, including the fragrance as described above, and, if necessary, suitably including the optional components.

The thus-produced heating tool is, in general, further packaged in the air-impermeable outer bag preventing permeation of oxygen to be provided or stored while maintaining an airtight state. In the heating tool of the present invention, since the exothermic composition generates heat upon contact with oxygen, it is important to prevent the heating tool from contacting oxygen during storage to prevent heat generation until usage. Upon usage, the heating tool of the present invention may be used by opening the outer bag, removing the heating tool from the outer bag, and bringing the exothermic composition into contact with oxygen to generate heat. The outer bag used herein is not particularly limited as long as it is an air-impermeable bag that does not allow permeation of oxygen.

Such a heating tool can be used for the purpose of heat retention, blood circulation promotion, fatigue alleviation, relaxation, etc. Therefore, it can be used as warming tools such as disposable body warmers, medical devices such as blood-circulation-improving tools, fatigue-alleviating tools, and warming treatment tools, fragrance tools, insect-repellent tools, etc. When the heating tool of the present invention contains a fragrance, the heating tool is, for example, referred to as a perfumed heating tool, etc. The heating tool of the present invention is considered to have additional effects depending on the effects (functions) of the fragrance and optional components.

Thus, since the heating tool of the present invention contains the metal ion sequestrant, unpleasant odors attributable to the exothermic composition can be effectively suppressed. Further, according to the present invention, even when the heating tool contains a fragrance, changes in or loss of aroma originating from the fragrance can be suppressed, making it possible to maintain the desired aroma. Furthermore, according to the present invention, even when the heating tool is used after storage, unpleasant odors can be effectively suppressed, and excellent aromatic properties can be exhibited. Still further, according to the heating tool of the present invention, exothermic effects sufficient as a heating tool can be exhibited.

When the heating tool of the present invention contains an oxidation accelerator, the desired effect can be obtained, and exothermic effects can be more efficiently exhibited. When the heating tool of the present invention contains an oxidation accelerator and a fragrance, changes in or loss of aroma originating from the fragrance can be more effectively suppressed, and desired aromatic properties can be maintained, by using the oxidation accelerator having an iodine adsorption of not higher than 400 mg/g on average. Further, the exothermic effects of a heating tool, particularly a disposable body warmer, can be more efficiently exhibited by using, in the heating tool of the present invention, an oxidation accelerator having a certain level of electronic conductivity. Furthermore, when the heating tool of the present invention uses an oxidation accelerator having an iodine adsorption of not higher than 400 mg/g on average and electronic conductivity, desired aromatic properties can be more effectively maintained, and the exothermic effects of a heating tool, particularly a disposable body warmer, can be more efficiently exhibited.

Since the heating tool of the present invention contains the metal ion sequestrant, even when the heating tool is stored for a long period of time while the fragrance for perfuming the heating tool and the exothermic composition are in contact, excellent aromatic properties can be obtained upon usage. Accordingly, in the heating tool of the present invention, the fragrance and the exothermic composition can exist in a state of being in contact with each other, or can exist in a state of not being in contact. In the heating tool of the present invention, when the fragrance is disposed outside of the container bag for the exothermic composition without being in direct contact with the exothermic composition, and is further packaged and stored in the air-impermeable outer bag, aroma may fill the space in the outer bag in some cases. Even in such a case, according to the heating tool of the present invention, changes in or loss of the fragrance in the exothermic composition can be suppressed or prevented. Therefore, according to the present invention, a heating tool having various configurations not limited by the arrangement relationship between the fragrance and the exothermic composition can be obtained.

According to the heating tool of the present invention, since the types of fragrances are not limited, desired fragrances can be widely used.

The present inventors considered that particular unpleasant odors attributable to the exothermic composition and changes in aroma are generated in the heating tool for the reasons described below. A transition metal ion or the like such as iron present in the exothermic composition or a transition metal in combination with other components in the exothermic composition form(s) a compound or a complex, and act(s) as a catalyst. This catalysis effect promotes addition reaction, substitution reaction, coupling reaction, etc., of various components present in the heating tool to change the various components to odor-emitting substances. In particular, a transition metal ion or the like, such as iron, appears to act on a component such as a water-absorbing resin (e.g., unsaturated low-molecular substances, such as monomers of sodium polyacrylate) to change the component to an unpleasant-odor-emitting substance. When the heating tool contains a fragrance, a transition metal ion or the like used as a catalyst appears to promote addition reaction, substitution reaction, coupling reaction, etc., to also change components constituting the fragrance to substances emitting odors different from the odors of the original components. The present invention was accomplished based on these findings, which were independently discovered by the inventors. Specifically, the present inventors found that the use of the metal ion sequestrant can suppress unpleasant odors attributable to the exothermic composition of the heating tool and change in aromatic notes during storage or use while not impairing the exothermic properties of the heating tool, and accomplished the present invention.

The above also indicates that the present invention provides a method for suppressing the generation of unpleasant odors and/or changes in aroma in a heating tool, the method comprising the step of housing an exothermic composition containing a metal ion sequestrant, an oxidizable metal powder, a water-soluble salt, and water in an air-permeable container bag. The present invention also provides a method for suppressing generation of unpleasant odors and/or changes in aroma in the heating tool, the method comprising the step of housing the exothermic composition further containing an oxidation accelerator and/or a water-retaining agent in an air-permeable container bag. The present invention further provides a method for suppressing the generation of unpleasant odors and/or changes in aroma in the heating tool, the method further comprising the step of incorporating a fragrance. Additionally, the present invention also provides a method for suppressing the generation of unpleasant odors and/or changes in aroma in the heating tool by using the heating tool. The present invention also provides a heating tool used in the method for suppressing the generation of unpleasant odors and/or changes in aroma in the heating tool. The present invention further provides use of the heating tool for producing the heating tool in which the generation of unpleasant odors and/or changes in aroma can be suppressed. The heating tool and each component used in these methods, and the addition amount of each component, production method, application method, etc., are explained in a similar manner as above.

EXAMPLES

The present invention is described below by means of Examples. However, the present invention is not limited to Examples provided below.

Test Example 1

(1) Production of Heating Tools (Examples 1 to 5)

Heating tools (Examples 1 to 5) having the structure shown in FIG. 4 or FIG. 1 were produced by the procedure described below.

First, the components described below were used in an exothermic composition.

Exothermic Composition
  Iron Powder (manufactured by DOWA IP Creation Co., Ltd., product name: DKP, average particle diameter: 100 μm)
  Carbon Black (manufactured by Mitsubishi Chemical Corp., product name: RCF, iodine adsorption: 144 mg/g, average particle diameter: 0.075 μm)
  Ethylenediaminetetraacetic Acid Trisodium Salt (manufactured by Kishida Chemical Co., Ltd., product name: Special-grade ethylenediaminetetraacetic acid trisodium salt (hydrate)
  Water
  Vermiculite (average particle diameter: about 500 μm)
  Water-Absorbing Polymer (acrylic acid polymer partial salt crosslinked product, average particle diameter: 250 μm)
  Common Salt Further, to produce heating tools containing a fragrance, the fragrances below were used.

Fragrances
  Floral (Fragrance Number: BR12942, manufactured by Ogawa & Co., Ltd.)
  Rose (Fragrance Number: OFR3386, manufactured by T. Hasegawa Co., Ltd.)
  Fruity (Fragrance Number: OFR3363, manufactured by T. Hasegawa Co., Ltd.)
  Soap (Fragrance Number: BR3906, manufactured by Ogawa & Co., Ltd.)

The above components of the exothermic composition were mixed to obtain a mixture. Herein, the proportions of the iron powder, the carbon black, the ethylenediaminetetraacetic acid trisodium salt, the water, the vermiculite, the water-absorbing polymer, and the common salt were 50 wt %, 20 wt %, 0.1 wt %, 20.4 wt %, 5 wt %, 2.5 wt %, and 2 wt %, respectively. The obtained mixture was housed and sealed in an air-permeable container bag (130×95 mm) made of a porous film (manufactured by Nitto Lifetech Corp., product name: Breathron) (e.g., 1 in FIG. 4) to which an air-impermeable adhesive sheet (manufactured by Nitto Lifetech Corp., product name: Nitotac) (e.g., 5 and 6 in FIG. 4) was partially attached, giving a heating tool (Example 1). The heating tool of Example 1 was then quickly packaged in an air-impermeable outer bag for a disposable body warmer. In this manner, a fragrance-free heating tool was produced.

Further, heating tools containing a fragrance were prepared as follows. The above components of the exothermic composition and each fragrance were mixed to obtain a mixture. Herein, the proportions of the iron powder, the carbon black, the ethylenediaminetetraacetic acid trisodium salt, the water, the vermiculite, the water-absorbing polymer, the common salt, and the fragrance were 50 wt %, 20 wt %, 0.1 wt %, 20.3 wt %, 5 wt %, 2.5 wt %, 2 wt %, and 0.1 wt %, respectively. The obtained mixture was housed and sealed in an air-permeable container bag (130×95 mm) made of a porous film to which an air-impermeable adhesive sheet was partially attached (e.g., 1, 5, and 6 in FIG. 1) in the same manner as in Example 1, giving heating tools. The obtained heating tools were then quickly packaged in an air-impermeable outer bag for a disposable body warmer.

Among these fragrances, a heating tool containing Floral was designated as Example 2, a heating tool containing Rose was designated as Example 3, a heating tool containing Fruity was designated as Example 4, and a heating tool containing Soap was designated as Example 5.

(2) Production of Heating Tools (Examples 6 to 10)

Heating tools (Examples 6 to 10) were produced in a similar manner except that a trisodium citrate (manufactured by Fuso Chemical Co., Ltd., product name: purified sodium citrate M) was used instead of the ethylenediaminetetraacetic acid trisodium salt. A fragrance-free heating tool was designated as Example 6, a heating tool containing Floral was designated as Example 7, a heating tool containing Rose was designated as Example 8, a heating tool containing Fruity was designated as Example 9, and a heating tool containing Soap was designated as Example 10.

(3) Production of Comparative Heating Tools (Comparative Examples 1 to 5)

As Comparative Examples, comparative heating tools (Comparative Examples 1 to 5) were produced in a manner similar to the methods used in Examples 1 to 5, except that a metal ion sequestrant was not used. In Comparative Example 1, the proportions of the iron powder, the carbon black, the water, the vermiculite, the water-absorbing polymer, and the common salt were 50 wt %, 20 wt %, 20.5 wt %, 5 wt %, 2.5 wt %, and 2 wt %, respectively. In Comparative Examples 2 to 5, the proportions of the iron powder, the carbon black, the water, the vermiculite, the water-absorbing polymer, the common salt, and the fragrance were 50 wt %, 20 wt %, 20.4 wt %, 5 wt %, 2.5 wt %, 2 wt %, and 0.1 wt %, respectively. A fragrance-free comparative heating tool was designated as Comparative Example 1, a comparative heating tool containing Floral was designated as Comparative Example 2, a comparative heating tool containing Rose was designated as Comparative Example 3, a comparative heating tool containing Fruity was designated as Comparative Example 4, and a comparative heating tool containing Soap was designated as Comparative Example 5.

(4) Evaluation of Heating Tools

The heating tools of Examples 1 to 10 and Comparative Examples 1 to 5 were evaluated as follows. Before and after storage, the outer bags were opened to remove the heating tools, and the intensities of aroma, changes in the aromatic notes, and the exothermal characteristics were evaluated. More specifically, before storing the heating tools of Examples 1 to 10 and Comparative Examples 1 to 5 (24 hours after the production), the air-impermeable outer bags were opened, and the intensities of aroma and the temperatures one hour after opening were evaluated. Further, the heating tools of Examples 1 to 10 and Comparative Examples 1 to 5 were stored in a thermostatic chamber at 50° C. in the presence of oxygen for 14 days, after which the outer bags were similarly opened, and the intensities of the aroma, changes in the aromatic notes, and the temperature one hour after opening were evaluated. The storage conditions correspond to storage at room temperature (25° C.) for 9 months.

More specifically, five subjects were asked to smell the aroma of the respective heating tools removed from the outer bags, and evaluate the intensities of the aroma and changes in the aromatic notes on a scale of 1 to 5 described below. The higher the value of the intensity of the aroma, the stronger the aroma. The lower the value of changes in the aromatic notes, the smaller the change in the aroma before and after storage. Further, simultaneously, the temperature of each heating tool was evaluated. The temperature herein is a value measured one hour after the opening of the outer bag and was evaluated as described below. A predetermined underlay material and covering material were laid on a warming portion defined in JIS S4100 (2007). The warming portion was heated to 30° C., and held within ±1° C. of that temperature. Meanwhile, the heating tool left in an atmosphere having the same temperature as the ambient temperature was caused to generate heat based on the method of use, and the temperature was measured.

Intensities of Aroma
1: Odorless
2: Slightly fragrant
3: Moderately fragrant
4: Strongly fragrant
5: Very strongly fragrant Changes in Aromatic Notes
1: No change
2: Slightly changed
3: Somewhat changed
4: Changed
5: Greatly changed (5) Results Table 1 shows evaluation results for the heating tools of Examples 1 to 10.

TABLE 1

| Test Example 1 | Initial Stage | | 50° C., 14 days later | | |
| --- | --- | --- | --- | --- | --- |
| | Aroma intensity | Temperature one hour after opening | Aroma intensity | Change in aromatic note | Temperature one hour after opening |
| Example 1 | 1.4 | 55 | 1.2 | 1.0 | 55 |
| Example 2 | 4.0 | 55 | 4.0 | 1.6 | 55 |
| Example 3 | 3.8 | 55 | 3.4 | 2.0 | 55 |
| Example 4 | 4.0 | 55 | 4.0 | 1.0 | 55 |
| Example 5 | 4.4 | 55 | 4.2 | 2.0 | 55 |
| Example 6 | 2.0 | 55 | 2.0 | 1.0 | 55 |
| Example 7 | 4.2 | 55 | 4.0 | 2.0 | 55 |
| Example 8 | 3.6 | 55 | 3.6 | 2.0 | 55 |
| Example 9 | 3.8 | 55 | 4.0 | 1.6 | 55 |
| Example 10 | 4.2 | 55 | 4.2 | 2.0 | 55 |

Table 2 shows evaluation results for the heating tools of Comparative Examples 1 to 5.

TABLE 2

| Test Example 1 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Comparative Example 1 | 3.6 | 55 | 3.2 | 4.2 | 55 |
| Comparative Example 2 | 4.2 | 55 | 3.2 | 4.0 | 55 |
| Comparative Example 3 | 4.0 | 55 | 3.0 | 4.2 | 55 |
| Comparative Example 4 | 3.8 | 55 | 3.2 | 4.4 | 55 |
| Comparative Example 5 | 4.2 | 55 | 4.0 | 4.2 | 55 |

As is clear from Table 1, among the heating tools containing a metal ion sequestrant, before storage ("initial stage" in the table), the aroma was hardly sensed in Examples 1 and 6, which were fragrance-free. Further, the aroma was distinctly sensed in Examples 2 to 5 and Examples 7 to 10 containing a fragrance. This difference was due to the presence or absence of fragrance in the heating tools, and the unpleasant odor attributable to the exothermic composition was not sensed. A similar tendency was also observed in Examples 1 to 10 after storage. It was also confirmed that the aromatic notes hardly changed after storage. In particular, in Examples 2 to 5 and Examples 7 to 10, only the aroma originating from the fragrance was sensed both before and after storage. Thus, their aromatic properties were not substantially changed, and were excellent.

Regarding the heat-generation temperatures, the temperatures of the respective heating tools one hour after opening were 55° C. both before and after storage, thus confirming that the heating tools of these Examples were sufficiently useful as heating tools, in particular, as disposable body warmers.

In contrast, for the metal-ion-sequestrant-free heating tools, as is clear from Table 2 showing the results of Comparative Example 1, a distinct smell was sensed both before and after storage, even though these heating tools did not contain a fragrance. This smell was an unpleasant odor attributable to the exothermic composition. Further, after storage, changes in the aromatic notes were significant in all of Comparative Examples 1 to 5, which were metal ion sequestrant-free. The changes in the aromatic notes were considered to derive from insufficient suppression of the unpleasant odor and alteration of the components, such as fragrances, of the heating tools.

This revealed that, by using a metal ion sequestrant, the unpleasant odor attributable to the exothermic composition can be effectively suppressed, and that the changes in the aromatic notes can also be effectively suppressed regardless of the presence or absence of the aroma. Further, it was also revealed that by using a metal ion sequestrant, the aromatic properties originating from the fragrances can be effectively retained, even after storage.

Test Example 2

(1) Production of Heating Tools (Examples 11 to 15)

Heating tools (Examples 11 to 15) having the structure shown in FIG. 4 or FIG. 1 were produced by the procedure described below.

First, the components described below were used in an exothermic composition.

Exothermic Composition
  Iron Powder (manufactured by DOWA IP Creation Co., Ltd., product name: DKP, average particle diameter: 100 μm)
  Activated Carbon (manufactured by Futamura Chemical Co., Ltd., product name: Taiko Kasseitan, iodine adsorption: 1050 mg/g, average particle diameter: 100 μm)
  Ethylenediaminetetraacetic Acid Trisodium Salt (manufactured by Kishida Chemical Co., Ltd., product name: Special-grade ethylenediaminetetraacetic acid trisodium salt (hydrate))
  Water
  Vermiculite (average particle diameter: about 500 μm)
  Water-Absorbing Polymer (acrylic acid polymer partial salt crosslinked product, average particle diameter: 250 μm)
  Common Salt The heating tools containing a fragrance were produced by using the above-stated four fragrances.

The components of the exothermic composition were mixed to obtain a mixture. Herein, the proportions of the iron powder, the activated carbon, the ethylenediaminetetraacetic acid trisodium salt, the water, the vermiculite, the water-absorbing polymer, and the common salt were 50 wt %, 20 wt %, 0.1 wt %, 20.4 wt %, 5 wt %, 2.5 wt %, and 2 wt %, respectively. The obtained mixture was housed and sealed in an air-permeable container bag (130×95 mm) made of a porous film to which an air-impermeable adhesive sheet was partially attached in a manner similar to the method used in Example 1, giving a heating tool (Example 11). The heating tool of Example 11 was then quickly packaged in an air-impermeable outer bag for a disposable body warmer. In this manner, a fragrance-free heating tool was produced.

Further, heating tools containing a fragrance were prepared as follows. The components of the exothermic composition and each fragrance were mixed to obtain a mixture. Herein, the proportions of the iron powder, the activated carbon, the ethylenediaminetetraacetic acid trisodium salt, the water, the vermiculite, the water-absorbing polymer, the common salt, and the fragrance were 50 wt %, 18 wt %, 0.1 wt %, 18.4 wt %, 4.5 wt %, 2.5 wt %, 2 wt %, and 4.5 wt %, respectively. The obtained mixture was housed and sealed in an air-permeable container bag (130×95 mm) made of a porous film to which an air-impermeable adhesive sheet was partially attached in a manner similar to the method in Example 11, giving heating tools. Each obtained heating tool was then quickly packaged in an air-impermeable outer bag for a disposable body warmer.

Among these fragrances, a heating tool containing Floral was designated as Example 12, a heating tool containing Rose was designated as Example 13, a heating tool containing Fruity was designated as Example 14, and a heating tool containing Soap was designated as Example 15.

(2) Production of Heating Tools (Examples 16 to 20)

Heating tools (Examples 16 to 20) were produced in a manner similar to the methods used in Examples 11 to 15, except that trisodium citrate (manufactured by Fuso Chemical Co., Ltd., product name: purified sodium citrate M) was used instead of the ethylenediaminetetraacetic acid trisodium salt. A fragrance-free heating tool was designated as Example 16, a heating tool containing Floral was designated as Example 17, a heating tool containing Rose was designated as Example 18, a heating tool containing Fruity was designated as Example 19, and a heating tool containing Soap was designated as Example 20.

(3) Production of Comparative Heating Tools (Comparative Examples 6 to 10)

As Comparative Examples, comparative heating tools (Comparative Examples 6 to 10) were produced in a manner similar to the methods used in Examples 11 to 15, except that a metal ion sequestrant was not used. In Comparative Example 6, the proportions of the iron powder, the activated carbon, the water, the vermiculite, the water-absorbing polymer, and the common salt were 50 wt %, 20 wt %, 20.5 wt %, 5 wt %, 2.5 wt %, and 2 wt %, respectively. Further, in Comparative Examples 7 to 10, the proportions of the iron powder, the activated carbon, the water, the vermiculite, the water-absorbing polymer, the common salt, and the fragrance were 50 wt %, 18 wt %, 18.5 wt %, 4.5 wt %, 2.5 wt %, 2 wt %, and 4.5 wt %, respectively. A fragrance-free comparative heating tool was designated as Comparative Example 6, a comparative heating tool containing Floral was designated as Comparative Example 7, a comparative heating tool containing Rose was designated as Comparative Example 8, a comparative heating tool containing Fruity was designated as Comparative Example 9, and a comparative heating tool containing Soap was designated as Comparative Example 10.

(4) Evaluation of Heating Tools

The heating tools of Examples 11 to 20 and Comparative Examples 6 to 10 were evaluated in a manner similar to the method of Test Example 1 in terms of the intensities of the aroma and the temperature one hour after opening before storage, as well as the intensities of the aroma, changes in the aromatic notes, and the temperature one hour after opening after the heating tools were stored in a thermostatic chamber at 50° C. in the presence of oxygen for 14 days.

(5) Results

Table 3 shows evaluation results for the heating tools of Examples 11 to 20.

TABLE 3

| Test Example 2 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Example 11 | 1.0 | 55 | 1.0 | 1.0 | 55 |
| Example 12 | 5.0 | 55 | 1.8 | 1.2 | 55 |
| Example 13 | 5.0 | 55 | 1.6 | 1.2 | 55 |
| Example 14 | 5.0 | 55 | 1.6 | 1.0 | 55 |
| Example 15 | 5.0 | 55 | 1.6 | 1.2 | 55 |
| Example 16 | 1.0 | 55 | 1.0 | 1.0 | 55 |
| Example 17 | 5.0 | 55 | 1.6 | 1.2 | 55 |
| Example 18 | 5.0 | 55 | 1.6 | 1.0 | 55 |
| Example 19 | 5.0 | 55 | 1.6 | 1.0 | 55 |
| Example 20 | 5.0 | 55 | 1.8 | 1.2 | 55 |

Table 4 shows evaluation results for the heating tools of Comparative Examples 6 to 10.

TABLE 4

| Test Example 2 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Comparative Example 6 | 1.0 | 55 | 1.0 | 1.0 | 55 |
| Comparative Example 7 | 5.0 | 55 | 1.4 | 3.0 | 55 |
| Comparative Example 8 | 5.0 | 55 | 1.6 | 2.2 | 55 |
| Comparative Example 9 | 5.0 | 55 | 1.4 | 2.0 | 55 |
| Comparative Example 10 | 5.0 | 55 | 1.2 | 1.2 | 55 |

As is clear from Table 3, before storage, aroma was hardly sensed in Examples 11 and 16, which were fragrance-free. In contrast, for the heating tools of Examples 12 to 15 and Examples 17 to 20 containing fragrances, a distinct aroma was sensed. This difference was due to the presence or absence of fragrance in the heating tools, and the unpleasant odor attributable to the exothermic composition was not sensed. Further, the aromas sensed in Examples 12 to 15 and Examples 17 to 20 emanated from the fragrances contained in the heating tools. In Examples 11 to 20, changes in the aromatic notes after storage were hardly detected, showing that their aromatic properties were not substantially changed and were excellent. Although the intensities of aroma decreased in Examples 12 to 15 and Examples 17 to 20 after storage, this is presumably due to adsorption of the aroma by the activated carbon having a high iodine-adsorption property. Regarding the heat-generation temperature, the temperatures of the respective heating tools one hour after opening were 55° C. both before and after storage, thus confirming that the heating tools of these Examples were sufficiently useful as heating tools, in particular, as disposable body warmers.

In contrast, for the metal-ion-sequestrant-free heating tools, there was a tendency for the changes in the aromatic notes to be significant after storage. The changes in the aromatic notes were presumably due to alteration of the components, such as fragrances, of the heating tools.

Further, although a decrease in the intensities of aroma was observed in Examples 12 to 15, Examples 17 to 20, and in Comparative Examples 7 to 10 after storage, as described above, the changes in the aromatic notes were significantly suppressed in Examples 12 to 15 and Examples 17 to 20. This revealed that the heating tools of Examples 12 to 15 and Examples 17 to 20 are capable of stably exhibiting desirable aromatic properties originating from the fragrances.

This shows that even with the use of activated carbon having a high iodine-adsorption property, it is possible to significantly suppress the changes in the aromatic notes by using a metal ion sequestrant. Thus, it was confirmed that a heating tool containing a metal ion sequestrant is superior to a metal-ion-sequestrant-free heating tool.

Test Example 3

(1) Production of Heating Tools (Examples 21 to 25)

Heating tools (Examples 21 to 25) having the structure shown in FIG. 4 or FIG. 1 were produced by the procedure described below.

First, the components described below were used in an exothermic composition.

Exothermic Composition
  Iron Powder (manufactured by DOWA IP Creation Co., Ltd., product name: DKP, average particle diameter: 100 μm)
  Bamboo Charcoal (manufactured by Kiriya Chemical Co., Ltd., product name: Takesumi Powder (bamboo charcoal powder), iodine adsorption 338 mg/g, average particle diameter: 50 μm)
  Ethylenediaminetetraacetic Acid Trisodium Salt (manufactured by Kishida Chemical Co., Ltd., product name: Special-grade ethylenediaminetetraacetic acid trisodium salt (hydrate))
  Water
  Vermiculite (average particle diameter: 500 μm)
  Water-Absorbing Polymer (acrylic acid polymer partial salt crosslinked product, average particle diameter: 250 μm)
  Common Salt The heating tools containing a fragrance were produced by using the above-stated four fragrances.

The components of the exothermic composition were mixed to obtain a mixture. Herein, the proportions of the iron powder, the bamboo charcoal, the ethylenediaminetetraacetic acid trisodium salt, the water, the vermiculite, the water-absorbing polymer, and the common salt were 50 wt %, 20 wt %, 0.1 wt %, 20.4 wt %, 5 wt %, 2.5 wt %, and 2 wt %, respectively. The obtained mixture was housed and sealed in an air-permeable container bag (130×95 mm) made of a porous film to which an air-impermeable adhesive sheet was partially attached in a manner similar to the method in Example 1, giving a heating tool (Example 21). The heating tool of Example 21 was then quickly packaged in an air-impermeable outer bag for a disposable body warmer. In this manner, a fragrance-free heating tool was produced.

Further, heating tools containing a fragrance were prepared as follows. The components of the exothermic composition and each fragrance were mixed to obtain a mixture. Herein, the proportions of the iron powder, the bamboo charcoal, the ethylenediaminetetraacetic acid trisodium salt, the water, the vermiculite, the water-absorbing polymer, the common salt, and the fragrance were 50 wt %, 20 wt %, 0.1 wt %, 20.3 wt %, 5 wt %, 2.5 wt %, 2 wt %, and 0.1 wt %, respectively. The obtained mixture was housed and sealed in an air-permeable container bag (130×95 mm) made of a porous film to which an air-impermeable adhesive sheet was partially attached in a manner similar to the method of Example 21, giving heating tools. Each of the obtained heating tools was then quickly packaged in an air-impermeable outer bag for a disposable body warmer.

Among these fragrances, a heating tool containing Floral was designated as Example 22, a heating tool containing Rose was designated as Example 23, a heating tool containing Fruity was designated as Example 24, and a heating tool containing Soap was designated as Example 25.

(2) Production of Heating Tools (Examples 26 to 30)

Heating tools (Examples 26 to 30) were produced in a manner similar to the methods used in Examples 21 to 25, except that trisodium citrate (manufactured by Fuso Chemical Co., Ltd., product name: purified sodium citrate M) was used instead of the ethylenediaminetetraacetic acid trisodium salt. A fragrance-free heating tool was designated as Example 26, a heating tool containing Floral was designated as Example 27, a heating tool containing Rose was designated as Example 28, a heating tool containing Fruity was designated as Example 29, and a heating tool containing Soap was designated as Example 30.

(3) Production of Comparative Heating Tools (Comparative Examples 11 to 15)

As Comparative Examples, comparative heating tools (Comparative Examples 11 to 15) were produced in a manner similar to the methods used in Examples 21 to 25, except that a metal ion sequestrant was not used. In Comparative Example 11, the proportions of the iron powder, the bamboo charcoal, the water, the vermiculite, the water-absorbing polymer, and the common salt were 50 wt %, 20 wt %, 20.5 wt %, 5 wt %, 2.5 wt %, and 2 wt %, respectively. Further, in Comparative Examples 12 to 15, the proportions of the iron powder, the bamboo charcoal, the water, the vermiculite, the water-absorbing polymer, the common salt, and the fragrance were 50 wt %, 20 wt %, 20.4 wt %, 5 wt %, 2.5 wt %, 2 wt %, and 0.1 wt %, respectively. A fragrance-free comparative heating tool was designated as Comparative Example 11, a comparative heating tool containing Floral was designated as Comparative Example 12, a comparative heating tool containing Rose was designated as Comparative Example 13, a comparative heating tool containing Fruity was designated as Comparative Example 14, and a comparative heating tool containing Soap was designated as Comparative Example 15.

(4) Evaluation of Heating Tools

The heating tools of Examples 21 to 30 and Comparative Examples 11 to 15 were evaluated in a manner similar to the method of Test Example 1 in terms of the intensities of the aroma and the temperature one hour after opening before storage, as well as the intensities of the aroma, changes in the aromatic notes, and the temperature one hour after opening after the heating tools were stored in a thermostatic chamber at 50° C. in the presence of oxygen for 14 days.

(5) Results

Table 5 shows evaluation results for the heating tools of Examples 21 to 30.

TABLE 5

| Test Example 3 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Example 21 | 1.4 | 50 | 1.0 | 1.0 | 50 |
| Example 22 | 4.0 | 50 | 1.8 | 1.6 | 50 |
| Example 23 | 4.0 | 50 | 2.4 | 2.0 | 50 |
| Example 24 | 4.0 | 50 | 1.8 | 1.4 | 50 |
| Example 25 | 4.4 | 50 | 2.0 | 2.0 | 50 |
| Example 26 | 1.4 | 50 | 1.0 | 1.0 | 50 |
| Example 27 | 4.2 | 50 | 1.8 | 2.2 | 50 |
| Example 28 | 3.8 | 50 | 2.4 | 2.2 | 50 |
| Example 29 | 3.8 | 50 | 1.8 | 1.6 | 50 |
| Example 30 | 4.2 | 50 | 2.0 | 2.0 | 50 |

Table 6 shows evaluation results for the heating tools of Comparative Examples 11 to 15.

TABLE 6

| Test Example 3 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Comparative Example 11 | 3.0 | 50 | 3.0 | 1.0 | 50 |
| Comparative Example 12 | 4.2 | 50 | 1.8 | 4.2 | 50 |
| Comparative Example 13 | 3.6 | 50 | 1.4 | 3.8 | 50 |
| Comparative Example 14 | 3.6 | 50 | 1.4 | 4.2 | 50 |
| Comparative Example 15 | 4.0 | 50 | 1.8 | 4.0 | 50 |

As shown in Table 5, before storage, the aroma was hardly sensed in Examples 21 and 26, which were fragrance-free. In contrast, before storage, a distinct aroma was sensed in Examples 22 to 25 and Examples 27 to 30 containing a fragrance. This difference was due to the presence or absence of fragrance in the heating tools. Further, the aromas sensed in Examples 22 to 25 and Examples 27 to 30 emanated from the fragrances contained in the heating tools. Further, in all of Examples 21 to 30, the unpleasant odor originating from the exothermic composition was not sensed.

Although a decrease in the intensities of aroma was detected in Examples 22 to 25 and Examples 27 to 30 after storage, the changes in the aromatic notes were significantly suppressed compared with the heating tools shown in Table 6, which were metal ion sequestrant-free. This revealed that, by using a metal ion sequestrant, it is possible to retain desirable aromatic properties even when the intensities of aroma decrease.

In Comparative Example 11, which was metal ion sequestrant-free, a distinct smell was sensed before storage, even though the heating tool did not contain a fragrance. This smell was an unpleasant odor attributable to the exothermic composition.

Regarding the heat generation temperatures, the temperatures of the heating tools one hour after opening were 50° C. both before and after storage, thus confirming that the heating tools of these Examples were sufficiently useful as a heating tool.

This revealed that the heating tool of the present invention containing a metal ion sequestrant can effectively suppress the unpleasant odor attributable to the exothermic composition, and also can effectively suppress changes in the aromatic notes, even when the intensities of aroma decrease after storage.

Test Example 4

(1) Production of Heating Tools (Examples 31 to 35)

Heating tools (Examples 31 to 35) having the structure shown in FIG. 4 or FIG. 1 were produced by the procedure described below.

First, the components described below were used in an exothermic composition.
Exothermic Composition
Iron Powder (manufactured by DOWA IP Creation Co., Ltd., product name: DKP, average particle diameter: 100 µm)
Charcoal (manufactured by Obayashi Sangyo Co., Ltd., product name: Subai, iodine adsorption: 63 mg/g, average particle diameter: 200 µm)
Ethylenediaminetetraacetic Acid Trisodium Salt (manufactured by Kishida Chemical Co., Ltd., product name: Special-grade ethylenediaminetetraacetic acid trisodium salt (hydrate))
Water
Vermiculite (average particle diameter: 500 µm)
Water-Absorbing Polymer (acrylic acid polymer partial salt crosslinked product, average particle diameter: 250 µm)
Common Salt The heating tools containing a fragrance were produced by using the above-stated four fragrances.

The components of the exothermic composition were mixed to obtain a mixture. Herein, the proportions of the iron powder, the charcoal, the ethylenediaminetetraacetic acid trisodium salt, the water, the vermiculite, the water-absorbing polymer, and the common salt were 50 wt %, 20 wt %, 0.1 wt %, 20.4 wt %, 5 wt %, 2.5 wt %, and 2 wt %, respectively. The obtained mixture was housed and sealed in an air-permeable container bag (130×95 mm) made of a porous film to which an air-impermeable adhesive sheet was partially attached in a manner similar to the method in Example 1, giving a heating tool (Example 31). The heating tool of Example 31 was then quickly packaged in an air-impermeable outer bag for a disposable body warmer. In this manner, a fragrance-free heating tool was produced.

Further, heating tools containing a fragrance were prepared as follows. The components of the exothermic composition and each fragrance were mixed to obtain a mixture. Herein, the proportions of the iron powder, the charcoal, the ethylenediaminetetraacetic acid trisodium salt, the water, the vermiculite, the water-absorbing polymer, the common salt, and the fragrance were 50 wt %, 20 wt %, 0.1 wt %, 20.3 wt %, 5 wt %, 2.5 wt %, 2 wt %, and 0.1 wt %, respectively. The obtained mixture was housed and sealed in an air-permeable container bag (130×95 mm) made of a porous film to which an air-impermeable adhesive sheet was partially attached in a manner similar to the method of Example 31, giving heating tools. Each of the obtained heating tools was then quickly packaged in an air-impermeable outer bag for a disposable body warmer.

Among these fragrances, a heating tool containing Floral was designated as Example 32, a heating tool containing Rose was designated as Example 33, a heating tool containing Fruity was designated as Example 34, and a heating tool containing Soap was designated as Example 35.

(2) Production of Heating Tools (Examples 36 to 40)

Heating tools (Examples 36 to 40) were produced in a manner similar to the methods used in Examples 31 to 35, except that a trisodium citrate (manufactured by Fuso Chemical Co., Ltd., product name: purified sodium citrate M) was used instead of the ethylenediaminetetraacetic acid trisodium salt. A fragrance-free heating tool was designated as Example 36, a heating tool containing Floral was designated as Example 37, a heating tool containing Rose was designated as Example 38, a heating tool containing Fruity was designated as Example 39, and a heating tool containing Soap was designated as Example 40.

(3) Production of Comparative Heating Tools (Comparative Examples 16 to 20)

As Comparative Examples, comparative heating tools (Comparative Examples 16 to 20) were produced in a manner similar to the methods used in Examples 31 to 35, except that a metal ion sequestrant was not used. In Comparative Example 16, the proportions of the iron powder, the charcoal, the water, the vermiculite, the water-absorbing polymer, and the common salt were 50 wt %, 20 wt %, 20.5 wt %, 5 wt %, 2.5 wt %, and 2 wt %, respectively. Further, in Comparative Examples 17 to 20, the proportions of the iron powder, the charcoal, the water, the vermiculite, the water-absorbing polymer, the common salt, and the fragrance were 50 wt %, 20 wt %, 20.4 wt %, 5 wt %, 2.5 wt %, 2 wt %, and 0.1 wt %, respectively. A fragrance-free comparative heating tool was designated as Comparative Example 16, a comparative heating tool containing Floral was designated as Comparative Example 17, a comparative heating tool containing Rose was designated as Comparative Example 18, a comparative heating tool containing Fruity was designated as Comparative Example 19, and a comparative heating tool containing Soap was designated as Comparative Example 20.

(4) Evaluation of Heating Tools

The heating tools of Examples 31 to 40 and Comparative Examples 16 to 20 were evaluated in a manner similar to the method of Test Example 1 in terms of the intensities of the aroma and the temperature one hour after opening before storage, as well as the intensities of the aroma, changes in the aromatic notes, and the temperature one hour after opening after the heating tools were stored in a thermostatic chamber at 50° C. in the presence of oxygen for 14 days.

(5) Results

Table 7 shows evaluation results for the heating tools of Examples 31 to 40.

TABLE 7

| Test Example 4 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Example 31 | 1.4 | 45 | 1.4 | 1.0 | 45 |
| Example 32 | 4.0 | 45 | 4.0 | 2.0 | 45 |
| Example 33 | 3.8 | 45 | 3.4 | 2.0 | 45 |
| Example 34 | 4.0 | 45 | 4.4 | 2.0 | 45 |
| Example 35 | 4.4 | 45 | 4.4 | 2.2 | 45 |
| Example 36 | 2.0 | 45 | 2.0 | 1.0 | 45 |
| Example 37 | 4.2 | 45 | 4.0 | 2.0 | 45 |
| Example 38 | 3.6 | 45 | 3.0 | 2.2 | 45 |
| Example 39 | 3.8 | 45 | 4.4 | 2.2 | 45 |
| Example 40 | 4.2 | 45 | 4.2 | 2.4 | 45 |

Table 6 shows evaluation results for the heating tools of Comparative Examples 16 to 20.

TABLE 8

| Test Example 4 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Comparative Example 16 | 3.0 | 45 | 3.0 | 1.0 | 45 |
| Comparative Example 17 | 4.2 | 45 | 3.2 | 4.0 | 45 |
| Comparative Example 18 | 4.0 | 45 | 3.0 | 3.8 | 45 |
| Comparative Example 19 | 3.8 | 45 | 3.4 | 4.2 | 45 |
| Comparative Example 20 | 4.2 | 45 | 3.6 | 3.8 | 45 |

As is clear from Table 7, the aroma was hardly sensed in Examples 31 and 36, which were fragrance-free. In contrast, for the heating tools of Examples 32 to 35 and Examples 37 to 40 containing a fragrance, a distinct aroma was sensed. In Examples 31 to 40, the intensities of aroma after storage did not decrease, and changes in the aromatic notes after storage was effectively suppressed. Both before and after storage, the aromas of Examples 32 to 35 and Examples 37 to 40 emanated from the fragrances contained in the heating tools; further, these aromas were substantially unaltered after storage. Further, in Examples 31 to 40, the unpleasant odor originating from the exothermic composition was not sensed.

Further, regarding the heat-generation temperatures, the temperatures of the respective heating tools one hour after opening were 45° C. both before and after storage, thus confirming that the heating tools of these Examples were sufficiently useful as heating tools.

In contrast, for the metal-ion-sequestrant-free heating tools, as is clear from Table 8 showing the results of Comparative Example 16, a distinct smell was sensed, even though these heating tools did not contain a fragrance. This smell was an unpleasant odor attributable to the exothermic composition. Further, in Comparative Examples 17 to 20, significant changes in the aromatic notes were sensed after storage. The significant changes in the aromatic notes were considered to derive from insufficient suppression of the unpleasant odor and alteration of the components, such as fragrances, of the heating tools.

This revealed that the heating tool of the present invention containing a metal ion sequestrant can effectively suppress the unpleasant odor attributable to the exothermic composition, and that it also effectively retains desirable aromatic properties. This further revealed that the heating tool of the present invention containing a metal ion sequestrant can effectively suppress the changes in the aromatic notes regardless of the presence or absence of the aroma. It was also revealed that the heating tool of the present invention exhibits a sufficient heat-retaining effect as a heating tool while ensuring such a superior effect.

Test Example 5

(1) Production of Heating Tools (Examples 41 to 45)

Heating tools (Examples 41 to 45) having the structure shown in FIG. 4 or FIG. 1 were produced by the procedure described below.

First, the components described below were used in an exothermic composition.

Exothermic Composition
  Iron Powder (manufactured by DOWA IP Creation Co., Ltd., product name: DKP, average particle diameter: 100 μm)
  Ethylenediaminetetraacetic Acid Trisodium Salt (manufactured by Kishida Chemical Co., Ltd., product name: Special-grade ethylenediaminetetraacetic acid trisodium salt (hydrate))
  Water
  Common Salt The heating tools containing a fragrance were produced by using the above-stated four fragrances.

The components of the exothermic composition were mixed to obtain a mixture. Herein, the proportions of the iron powder, the ethylenediaminetetraacetic acid trisodium salt, the water, and the common salt were 70 wt %, 0.1 wt %, 14.9 wt %, and 15 wt %, respectively. The obtained mixture was housed and sealed in an air-permeable container bag (130×95 mm) made of a porous film to which an air-impermeable adhesive sheet was partially attached in a manner similar to the method of Example 1, giving a heating tool (Example 41). The heating tool of Example 41 was then quickly packaged in an air-impermeable outer bag for a disposable body warmer. In this manner, a fragrance-free heating tool was produced.

Further, heating tools containing a fragrance were prepared as follows. The components of the exothermic composition and each fragrance were mixed to obtain a mixture. Herein, the proportions of the iron powder, the ethylenediaminetetraacetic acid trisodium salt, the water, the common salt, and the fragrance were 70 wt %, 0.1 wt %, 14.8 wt %, 15 wt %, and 0.1 wt %, respectively. The obtained mixture was housed and sealed in an air-permeable container bag (130×95 mm) made of a porous film to which an air-impermeable adhesive sheet was partially attached in a manner similar to the method of Example 41, giving heating tools. Each of the obtained heating tools was then quickly packaged in an air-impermeable outer bag for a disposable body warmer.

Among these fragrances, a heating tool containing Floral was designated as Example 42, a heating tool containing Rose was designated as Example 43, a heating tool containing Fruity was designated as Example 44, and a heating tool containing Soap was designated as Example 45.

(2) Production of Heating Tools (Examples 46 to 50)

Heating tools (Examples 46 to 50) were produced in a manner similar to the methods used in Examples 41 to 45, except that a trisodium citrate (manufactured by Fuso Chemical Co., Ltd., product name: purified sodium citrate M) was used instead of the ethylenediaminetetraacetic acid trisodium salt. A fragrance-free heating tool was designated as Example 46, a heating tool containing Floral was designated as Example 47, a heating tool containing Rose was designated as Example 48, a heating tool containing Fruity was designated as Example 49, and a heating tool containing Soap was designated as Example 50.

(3) Production of Comparative Heating Tools (Comparative Examples 21 to 25)

As Comparative Examples, comparative heating tools (Comparative Examples 21 to 25) were produced in a manner similar to the methods used in Examples 41 to 45, except that the metal ion sequestrant was not used. In Comparative Example 21, the proportions of the iron powder, the water, and the common salt were 70 wt %, 15 wt %, and 15 wt %, respectively. In Comparative Examples 22 to 25, the proportions of the iron powder, the water, the common salt, and the fragrance were 70 wt %, 14.9 wt %, 15 wt %, and 0.1 wt %, respectively. A fragrance-free comparative heating tool was designated as Comparative Example 21, a comparative heating tool containing Floral was designated as Comparative Example 22, a comparative heating tool containing Rose was designated as Comparative Example 23, a comparative heating tool containing Fruity was designated as Comparative Example 24, and a comparative heating tool containing Soap was designated as Comparative Example 25.

(4) Evaluation of Heating Tools

The heating tools of Examples 41 to 50 and Comparative Examples 21 to 25 were evaluated in a manner similar to the method of Test Example 1 in terms of the intensities of the aroma and the temperature one hour after opening before storage, as well as the intensities of the aroma, changes in the aromatic notes, and the temperature one hour after opening after the heating tools were stored in a thermostatic chamber at 50° C. in the presence of oxygen for 14 days.

(5) Results

Table 9 shows evaluation results for the heating tools of Examples 41 to 50.

TABLE 9

| Test Example 5 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Example 41 | 1.2 | 41 | 1.2 | 1.0 | 41 |
| Example 42 | 4.2 | 41 | 4.2 | 1.0 | 41 |
| Example 43 | 4.2 | 41 | 4.8 | 1.0 | 41 |
| Example 44 | 4.6 | 41 | 4.6 | 1.0 | 41 |
| Example 45 | 4.6 | 41 | 4.6 | 2.0 | 41 |
| Example 46 | 1.4 | 41 | 1.4 | 1.0 | 41 |
| Example 47 | 4.2 | 41 | 4.2 | 1.2 | 41 |
| Example 48 | 4.2 | 41 | 4.8 | 1.0 | 41 |
| Example 49 | 4.6 | 41 | 4.6 | 1.0 | 41 |
| Example 50 | 4.6 | 41 | 4.6 | 2.0 | 41 |

Table 10 shows evaluation results for the heating tools of Comparative Examples 21 to 25.

TABLE 10

| Test Example 5 | Initial Stage | | 50° C., 14 days later | | |
|---|---|---|---|---|---|
| | Aroma intensity | Temperature one hour after opening | Aroma intensity | Change in aromatic note | Temperature one hour after opening |
| Comparative Example 21 | 2.0 | 41 | 2.0 | 1.0 | 41 |
| Comparative Example 22 | 4.2 | 41 | 3.6 | 2.0 | 41 |
| Comparative Example 23 | 4.2 | 41 | 4.2 | 1.6 | 41 |
| Comparative Example 24 | 4.6 | 41 | 4.2 | 1.6 | 41 |
| Comparative Example 25 | 4.6 | 41 | 4.0 | 2.2 | 41 |

As is clear from Table 9, before storage, the aroma was hardly sensed in Examples 41 and 46, which were fragrance-free. In contrast, for the heating tools of Examples 42 to 45 and Examples 47 to 50 containing a fragrance, a distinct aroma was sensed. In Examples 41 to 50, the intensities of aroma after storage did not decrease, and changes in the aromatic notes after storage was effectively suppressed. Both before and after storage, the aromas of Examples 42 to 45 and Examples 47 to 50 emanated from the fragrances contained in the heating tools; further, these aromas were not substantially altered after storage. Further, in Examples 41 to 50, the unpleasant odor originating from the exothermic composition was not sensed.

Regarding the heat-generation temperatures, the temperatures of the respective heating tools one hour after opening were 41° C. both before and after storage, thus confirming that the heating tools of these Examples were sufficiently useful as heating tools.

In contrast, for the metal-ion-sequestrant-free heating tools, as is clear from Table 10 showing the results of Comparative Example 21, a smell was sensed both before and after storage, even though these heating tools did not contain a fragrance. This smell was an unpleasant odor originating from the exothermic composition. Further, changes in the aromatic notes were more significant in Comparative Examples 22 to 25 than in Examples 41 to 50. This is considered to be due to insufficient suppression of the unpleasant odor and alteration of the components, such as fragrances, of the heating tools.

This revealed that the heating tool of the present invention containing a metal ion sequestrant can effectively suppress the unpleasant odor attributable to the exothermic composition, and that, when the heating tool contains a fragrance, it also effectively retains desirable aromatic properties. This further revealed that the heating tool of the present invention containing a metal ion sequestrant can effectively suppress the changes in the aromatic notes regardless of the presence or absence of the aroma, and that this effect is ensured regardless of the presence or absence of oxidation accelerator or water-retaining agent, and regardless of the degree of the iodine-adsorption property or the electrical conductivity of the oxidation accelerator. Further, this also revealed that the heating tool of the present invention containing a metal ion sequestrant exhibits a sufficient heat-retaining effect as a heating tool while ensuring such superior effects.

Figure 2:
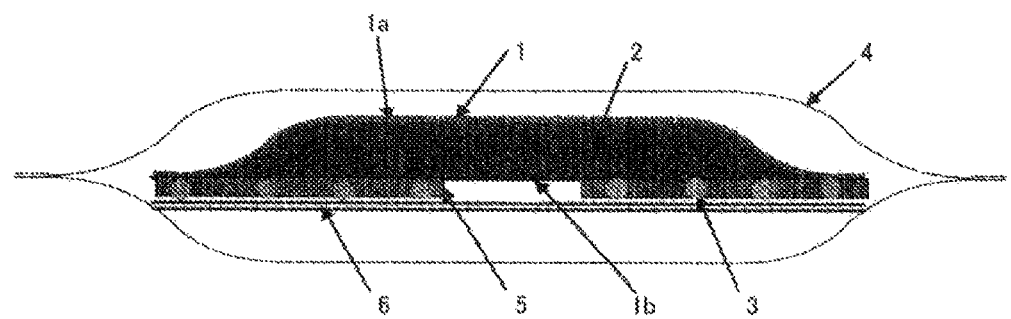
FIG. 2 is an example of a stick-on type heating tool packaged in an outer bag. The air-permeable container bag illustrated in FIG. 2 is a model drawing of a container bag having an air-permeable portion at one side and an air-impermeable portion at the other side.
Figure 3:
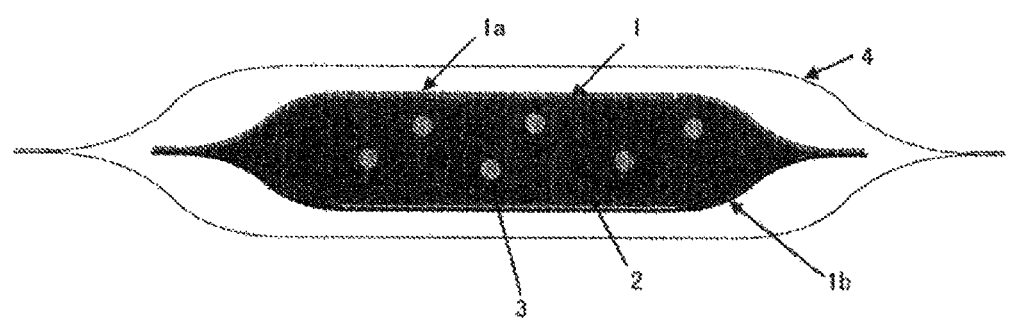
FIG. 3 is an example of a heating tool packaged in an outer bag. The air-permeable container bag illustrated in FIG. 3 is a model drawing of a container bag having an air-permeable portion at one side and an air-impermeable portion at the other side.
Figure 4:
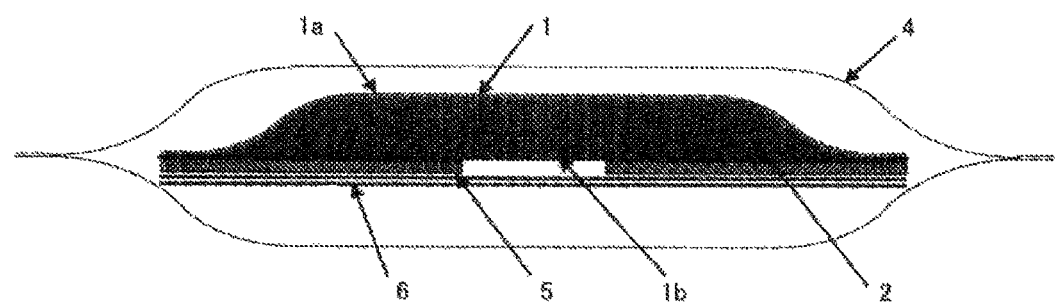
FIG. 4 is an example of a stick-on type heating tool packaged in an outer bag. The air-permeable container bag illustrated in FIG. 4 is a model drawing of a container bag having an air-permeable portion at one side and an air-impermeable portion at the other side.

The heating tools of Examples 1 to 50, which have the structure shown in FIG. 2 or FIG. 3 instead of the structure shown in FIG. 1 or FIG. 4, also exhibit the superior effects, as well as the above-described Examples.

DESCRIPTION OF THE REFERENCE NUMERALS

1. Air-permeable container bag (1a: air-permeable portion, 1b: air-impermeable portion)
2. Exothermic composition
3. Fragrance
4. Air-impermeable outer bag
5. Adhesive compound
6. Release paper

The invention claimed is:

1. A heating tool comprising an exothermic composition containing a metal ion sequestrant, an oxidizable metal powder, a water-soluble salt, and water,
   wherein at least the exothermic composition is housed in an air-permeable container bag.

2. The heating tool according to claim 1, further comprising an oxidation accelerator and/or a water-retaining agent.

3. The heating tool according to claim 2, wherein the oxidation accelerator is at least one member selected from the group consisting of carbon black, graphite, activated carbon, coal, charcoal, bamboo charcoal, acetylene black, and charcoal made from waste coffee grounds.

4. The heating tool according to claim 3, wherein the oxidation accelerator has an iodine adsorption of not higher than 400 mg/g on average.

5. The heating tool according to claim 2, wherein the oxidation accelerator has an iodine adsorption of not higher than 400 mg/g on average.

6. The heating tool according to claim 2, wherein the oxidation accelerator has electrical conductivity.

7. The heating tool according to claim 2, wherein the proportion of the oxidation accelerator in the exothermic composition is 1 to 30 wt %.

8. The heating tool according to claim 2, further comprising a fragrance.

9. The heating tool according to claim 1, further comprising a fragrance.

10. The heating tool according to claim 9, wherein the fragrance is contained in an amount of 0.0001 to 20 parts by weight per 100 parts by weight of the exothermic composition.

11. The heating tool according to claim 9, wherein the fragrance is contained in an amount of 0.0003 to 500 parts by weight per 100 parts by weight of the oxidation accelerator contained in the exothermic composition.

12. The heating tool according to claim 9, wherein the fragrance is housed in the air-permeable container bag.

13. The heating tool according to claim 9, wherein the fragrance is supported on a carrier.

14. The heating tool according to claim 9, wherein the oxidation accelerator is at least one member selected from the group consisting of carbon black, graphite, activated carbon, coal, charcoal, bamboo charcoal, acetylene black, and charcoal made from waste coffee grounds.

15. The heating tool according to claim 9, wherein the oxidation accelerator has an iodine adsorption of not higher than 400 mg/g on average.

16. The heating tool according to claim 1, wherein the metal ion sequestrant is at least one member selected from the group consisting of aminocarboxylic acid-based metal ion sequestrants, phosphonic acid-based metal ion sequestrants, condensed phosphoric acid-based metal ion sequestrants, carboxylic acid-based metal ion sequestrants, and substances having an ability to adsorb metal ions.

17. The heating tool according to claim 1, wherein the proportion of the metal ion sequestrant in the exothermic composition is 0.0001 to 10 wt %.

18. The heating tool according to claim 1, wherein the amount of the metal ion sequestrant contained in the exothermic composition is 0.0002 to 20 parts by weight per 100 parts by weight of the oxidizable metal powder.

19. The heating tool according to claim 1, wherein the heating tool is used in a method for suppressing the generation of unpleasant odors and/or changes in aroma in a heating tool.

20. A method for suppressing the generation of unpleasant odors and/or changes in aroma in a heating tool,
   the method comprising a step of housing an exothermic composition containing a metal ion sequestrant, an oxidizable metal powder, a water-soluble salt, and water in an air-permeable container bag.

* * * * *